United States Patent
Van Hoek et al.

(10) Patent No.: US 9,428,776 B2
(45) Date of Patent: *Aug. 30, 2016

(54) FERMENTATION PROCESS USING SPECIFIC OXYGEN UPTAKE RATES AS A PROCESS CONTROL

(71) Applicant: Cargill Incorporated, Wayzata, MN (US)

(72) Inventors: Pim Van Hoek, Minnetonka, MN (US); Aristos Aristidou, Maple Grove, MN (US); Brian J. Rush, Minneapolis, MN (US)

(73) Assignee: Cargill Incorporated, Wayzata, MN (US)

( * ) Notice: Subject to any disclaimer, the term of this patent is extended or adjusted under 35 U.S.C. 154(b) by 15 days.

This patent is subject to a terminal disclaimer.

(21) Appl. No.: 14/479,309

(22) Filed: Sep. 6, 2014

(65) Prior Publication Data

US 2014/0377794 A1  Dec. 25, 2014

Related U.S. Application Data

(60) Continuation of application No. 13/078,128, filed on Apr. 1, 2011, now Pat. No. 8,828,707, which is a continuation of application No. 11/707,188, filed on Feb. 14, 2007, now Pat. No. 7,939,298, which is a division of application No. 10/449,911, filed on May 30, 2003, now Pat. No. 7,232,664.

(60) Provisional application No. 60/384,333, filed on May 30, 2002.

(51) Int. Cl.
| | |
|---|---|
| *C12P 21/00* | (2006.01) |
| *C12P 7/56* | (2006.01) |
| *C12N 1/16* | (2006.01) |
| *C12N 9/04* | (2006.01) |
| *C12N 15/81* | (2006.01) |
| *C12P 7/62* | (2006.01) |
| *C12Q 1/02* | (2006.01) |

(52) U.S. Cl.
CPC . *C12P 7/56* (2013.01); *C12N 1/16* (2013.01); *C12N 9/0006* (2013.01); *C12N 15/815* (2013.01); *C12P 7/625* (2013.01); *C12Q 1/02* (2013.01); *G01N 2333/39* (2013.01); *Y02P 20/52* (2015.11)

(58) Field of Classification Search
None
See application file for complete search history.

(56) References Cited

U.S. PATENT DOCUMENTS

| | | |
|---|---|---|
| 7,232,664 B2 | 6/2007 | Van Hoek |
| 7,939,298 B2 | 5/2011 | Van Hoek |
| 8,828,707 B2 | 9/2014 | Van Hoek |

FOREIGN PATENT DOCUMENTS

| | | |
|---|---|---|
| WO | 0071738 A | 11/2000 |
| WO | 0242471 A | 5/2002 |

OTHER PUBLICATIONS

Porro et al., "Development of Metabolically Engineered Saccharomyces Cerevisiae Cells for the Production of Lactic Acid", Biotechnol. Prog. May-Jun. 1995 11(3), p. 294-8.
Porro et al., "Replacement of a Metabolic Pathway for Large-Scale Production of Lactic Acid from Engineered Yeasts", App. Environ. Microbiol. Sep. 1999 65(9), p. 4211-5.
Bianchi et al., "Efficient homolactic fermentation by Kluyveromyces lactis strains defective in pyruvate utilizatoin and transformed with the heterologous LDH gene", App. Environ. Microbiol. Dec. 2001 67(12) p. 6521-5.
Carplus 1995_627242, Hack et al., "The use of oxygen uptake rate to optimize air feed rate to a continuous ethanol fermenation".
Doig et al., "Large scale productoin of cyclohexanone monooxygenase from *Escherichia coli* TOP10 pQR239", Enzyme and Microbiol. Technology 28 (2001) 265-274.
Verduyn et al., "Effect of benzoic acid on metabolic fluxes in yeast . . . ", Yeast 8, 501-517 (1992).
Hack et al., "The effect of oxygen transfer rate on continuous ethanol fermentation by Kluyveromyces marxianus", Prehrambenoteknol. bioteknol. rev. 33 (4) 151-154 (1995).

*Primary Examiner* — Celine Qian
(74) *Attorney, Agent, or Firm* — Gary C Cohn PLLC

(57) ABSTRACT

Specific oxygen uptake (OUR) is used as a process control parameter in fermentation processes. OUR is determined during at least the production phase of a fermentation process, and process parameters are adjusted to maintain the OUR within desired ranges. The invention is particularly applicable when the fermentation is conducted using a microorganism having a natural PDC pathway that has been disrupted so that it no longer functions. Microorganisms of this sort often produce poorly under strictly anaerobic conditions. Microaeration controlled by monitoring OUR allows the performance of the microorganism to be optimized.

4 Claims, 1 Drawing Sheet

FERMENTATION PROCESS USING SPECIFIC OXYGEN UPTAKE RATES AS A PROCESS CONTROL

This application is a continuation of application Ser. No. 13/178,128, filed 1 Apr. 2011, now U.S. Pat. No. 8,828,707, which is a continuation of application Ser. No. 11/707,188, filed 14 Feb. 2007, now U.S. Pat. No. 7,939,298, which is a divisional of application Ser. No. 10/449,911, filed May 30, 2003, now U.S. Pat. No. 7,232,664, and claims priority to U.S. Provisional application no. 60/384,333, filed May 30, 2002.

This invention was made with U.S. Government support under Contract No. DE-FC-36-00GO10598, awarded by the Department of Energy. The U.S. government has certain rights in this invention.

BACKGROUND OF THE INVENTION

Lactic acid has wide industrial applicability including uses in chemical processing and synthesis, cosmetics, pharmaceuticals, plastics, and food production. Most industrial scale processes for making lactic acid are fermentation processes. Various lactic acid-producing bacteria have been used in those fermentation processes.

Recent research has investigated the use of recombinant yeast strains in lactic acid fermentation processes. Recombinant yeast potentially can provide several advantages over bacterial fermentations. Some yeast strains are more resistant to higher temperatures. This potentially allows for higher temperature fermentations, which can translate to faster rates of fermentations. Better resistance to high temperature can make it easier to purge a fermentation medium of contaminating microbes, as the medium can simply be heated to a temperature at which the unwanted species die off but the desired species can tolerate. Lactic acid-producing bacteria such as *lactobacilli* require a complex fermentation medium in order to produce efficiently. The complexity of the fermentation medium increases raw materials costs and makes it more difficult and expensive to separate the lactic acid from the medium. Using recombinant yeast offers the possibility of reducing costs by using a simplified fermentation medium.

Porro and coworkers have attempted to engineer a lactic-acid producing yeast by inserting an exogenous LDH (lactate dehydrogenase) gene into yeast cells from the species *S. cerevisiae*, *K. lactic*, *T. delbrueckii* and *Z. bailii*, and disrupting the cell's natural pyruvate pathway. See Porro et al., "Development of metabolically engineered *Saccharomyces cerevisiae* cells for the production of lactic acid", *Biotechnol. Prog.* 1995 May-June; 11(3): 294-8; Porro et al., "Replacement of a metabolic pathway for large-scale production of lactic acid from engineered yeasts", *App. Environ. Microbiol.* 1999 September:65(9):4211-5; Bianchi et al., "Efficient homolactic fermentation by *Kluyveromyces lactis* strains defective in pyruvate utilization and transformed with the heterologous LDH gene", *App. Environ. Microbiol.* 2001 December; 67(12)5621-5. Porro was able to produce a recombinant yeast that produces lactic acid, but the strains did not perform nearly well enough for implementation in any commercial process. To qualify for use in an industrial environment, the strain must generate good yields of lactic acid (i.e., high conversion of the substrate to lactic acid) and high productivity (i.e., rapid metabolism of the substrate to lactic acid). The yeast preferably is able to tolerate a medium having a high titer of lactic acid.

More recently, Rajgarhia and coworkers have created recombinant yeast that exhibits higher yields and productivities than those of Porro. See, for example, WO 00/71738, WO 02/42471 and PCT/US02/16223. Rajgarhia's work as described in WO 00/71738 attempts to take advantage of the so-called "Crabtree negative" phenotype exhibited by certain species of yeast. The Crabtree effect is defined as the occurrence of fermentative metabolism under aerobic conditions due to the inhibition of oxygen consumption by a microorganism when cultured at high specific growth rates (long-term effect) or in the presence of high concentrations of glucose (short-term effect). Crabtree negative phenotypes do not exhibit this effect, and are thus able to consume oxygen even in the presence of high concentrations of glucose or at high growth rates. Thus, cultures of Crabtree negative microorganisms, in theory at least, can be converted from a growth phase to a fermentation (production) phase through manipulation of oxygen supply. In the presence of significant aeration, the microorganisms grow to produce biomass and $CO_2$, whereas under anaerobic conditions, the cells instead ferment the available substrate to produce lactic acid or other fermentation products.

We have found, however, that certain strains do not ferment as efficiently as desired under strictly anaerobic conditions. This is true, for example, in engineered yeast strains in which the pyruvate decarboxylase (PDC) pathway is deleted or disrupted. However, the use of such engineered species is otherwise highly desirable in lactic acid fermentations (as well as others in which the desired product is not ethanol), as disruption of the PDC pathway reduces the amount of ethanol that is produced. Accordingly, it would be desirable to provide an improved fermentation process in which a strain that does not ferment efficiently under strictly anaerobic conditions can produce a desired fermentation product economically.

SUMMARY OF THE INVENTION

Figure 1:
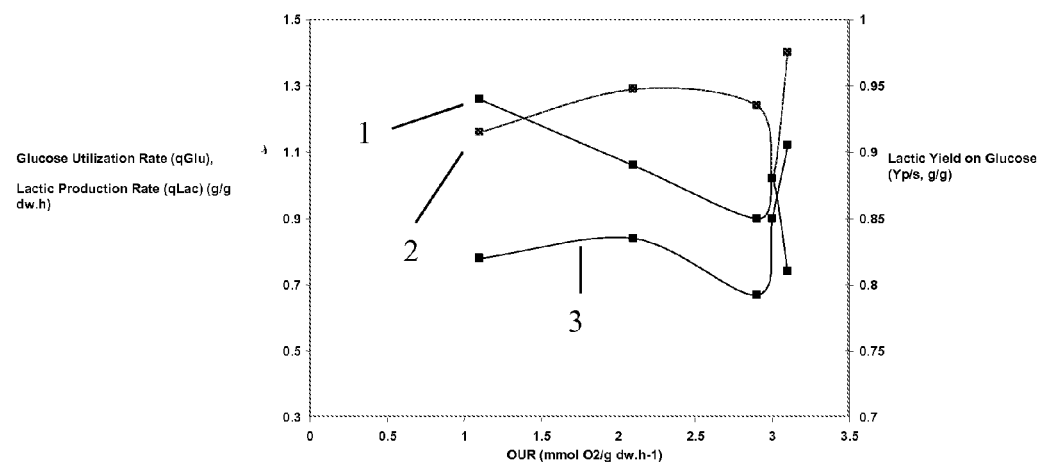
FIG. 1 is a graph illustrating the effect of OUR on glucose consumption, lactic acid production and yield for a certain genetically modified *K. marxianus* species.

In one aspect, this invention is a fermentation process wherein specific oxygen uptake rate is monitored during a production phase of the fermentation process, and at least one operating parameter is controlled in response to the measured oxygen uptake rate.

In another aspect, this invention is method of conducting a fermentation process in a fermentation medium comprising a fermenting microorganism, a substrate that is fermentable by the microorganism, the fermentation exhibiting a quantity of dissolved oxygen (DO) and a specific oxygen uptake (OUR) during the fermentation, comprising a) measuring the OUR during a production phase of a fermentation;

b) adjusting aeration conditions such that the OUR is maintained within a predetermined range while maintaining the DO at less than 1% of the saturation amount during the production phase of the fermentation.

In a third aspect, this invention is a process comprising
a) determining an optimum range of OUR values at which a fermenting microorganism ferments a carbohydrate to a desired fermentation product;
b) growing the microorganism in a medium comprising a carbohydrate that the cell is capable of metabolizing and one or more nutrients, while aerating the medium such that the cells as the cells grow and reproduce, the (DO) in the medium is reduced to less than 1% of the saturation amount and the cells exhibit a specific oxygen uptake rate of at least 10 mmol $O_2$/g dry weight of cells/hour (mmol $O_2$/gdw/h); and then
c) culturing the microorganism in a buffered medium under fermentation conditions including microaeration conditions sufficient to provide the culture with a specific oxygen uptake rate (OUR) within the optimum range.

This invention is in another aspect a fermentation process comprising
a) growing engineered yeast cells having a disrupted PDC pathway and an exogenous gene which allows the cell to produce a desired fermentation product in a medium comprising a carbohydrate that the cell is capable of metabolizing, while aerating the medium such that the cells as the cells grow and reproduce, the quantity of dissolved oxygen in the medium is reduced to less than 1% of saturation and the cells exhibit a specific oxygen uptake rate of at least 10 mmol $O_2$/g dry weight of cells/hour (mmol $O_2$/gdw/h); and then
b) culturing the cells in a buffered medium under fermentation conditions including microaeration conditions sufficient to provide the culture with a specific oxygen uptake rate (OUR) of about 0.8 to about 3.0 mmol $O_2$/gdw/h.

Surprisingly, the use of microaeration conditions using oxygen uptake rates as a process control parameter allows the fermentation process to be optimized, balancing high yields to the desired fermentation product with good production rates. OUR measurements can be used to establish and control certain parameters of the fermentation process in order to maintain optimum conditions during a production phase of a fermentation process.

DETAILED DESCRIPTION OF THE INVENTION

OUR is the rate of consumption of oxygen ($O_2$) per unit dry weight of the production microorganism per unit time. OUR is conveniently determined from the amount of oxygen that is consumed per unit time, and from the mass of the cells during that time period. Oxygen consumption is conveniently determined by measuring the amount of oxygen supplied to and removed from the fermentation vessel per unit time. OUR is then determined by dividing the oxygen consumption by the mass (dry weight) of the biomass in the broth. The weight of biomass can be determined by taking a sample and measuring the concentration of cells (w/v) and multiplying by the total broth volume. The amount of supplied oxygen can be straightforwardly measured by monitoring aeration rates. The amount of oxygen leaving the fermentation vessel can be measured using various analytical methods, of which mass spectroscopy is particularly useful. The difference between oxygen supplied and oxygen removed is the amount consumed by the cells. OUR is calculated by dividing oxygen consumption by the dry weight of the cells and by unit time. It is conveniently expressed in units of mmol $O_2$/grams cells (dry weight)/hour.

In its most general aspect, the invention involves measuring OUR during the production phase of a fermentation, and controlling at least one parameter of the fermentation in response to the measured OUR values. The parameter which is controlled in response to the measured OUR will typically be related to the aeration of the fermentation broth, such as aeration rates, agitation rates, aeration gas composition (increasing or decreasing oxygen concentration in the gas, for example), or some other parameter that affects the rate at which the microorganisms in the broth consume oxygen.

In a preferred aspect of the invention, fermenting cells are cultured under various aeration conditions to empirically establish an optimum range of OUR for the particular type of cell. The range of OUR that is optimum generally will take into account several factors, of which three tend to be paramount: yield of the desired fermentation product from the fermentation substrate (usually expressed in grams product/grams substrate consumed), specific productivity of the desired fermentation product (usually expressed in weight product/weight dry cell weight/unit time), and substrate consumption rates (usually expressed in weight of substrate consumed/unit time). These factors are not usually all optimized under the same aeration conditions. For example, substrate consumption rates sometimes increase with increasing OUR, but yields tend to drop, thereby counterbalancing faster production rates with greater yield losses and hurting the overall economics of the process. The establishment of an optimum range of OUR values generally will involve balancing rates with yield to optimize the overall process economics. Once a desired range of OUR values is established, fermentation conditions are selected in a production phase of a fermentation to establish and maintain the OUR within that range. As before, OUR is measured during the process and one or more fermentation parameters are controlled so that OUR is maintained within the range.

During this production phase, the concentration of dissolved oxygen is maintained at approximately zero, which reflects the condition that the cells are consuming oxygen at approximately the same rate at which it is becoming dissolved into the fermentation broth. The concentration of dissolved oxygen during the production phase is generally less than 1% of the saturation amount (i.e., the maximum amount that can be dissolved in the broth under the conditions of temperature and pressure that are used). Typically, dissolved oxygen contents of less than about 10 µmoles/L, more preferably less than about 5 µmoles/L, are suitable. Most preferably, the dissolved oxygen content is essentially zero. Dissolved oxygen is conveniently measured using an oxygen electrode with a gas-permeable membrane (Clark electrode), such as that manufactured by Ingold and sold by B Braun under part numbers 33182418 or 33182400. Operation at dissolved oxygen contents below the limit of detection of instruments such as these is considered to reflect a dissolved oxygen concentration of approximately zero for purposes of this invention.

In an especially preferred aspect of this invention, a microorganism is cultured under different growth and production conditions. In the growth phase, the microorganism is grown aerobically. The cells are grown in a medium that contains water, a carbohydrate that the cell can metabolize in both the growth and the production phases, and various nutrients as described more fully below. The aeration conditions are selected such that (1) the cells exhibit a specific oxygen uptake rate (OUR) of at least 10 mmol $O_2$/gdw/h and (2) at the end of the growth phase, and the concentration of dissolved oxygen (DO) in the medium is reduced to less than 1% of the saturation amount while maintaining an OUR of at least 10 mmol $O_2$/gdw/h. The OUR is preferably at least 15 and more preferably at least 18 mmol $O_2$/gdw/h. During the growth phase, the OUR is most preferably as high as the cells can generate. The maximum OUR therefore will depend somewhat on the particular engineered yeast cell that is used. In general, the maximum OUR is expected to be about 20-30 mmol $O_2$/gdw/h. *K. marxianus* cells having a PDC disruption and exogenous LDH gene tend to exhibit a maximum OUR in the range of about 20-22 mmol $O_2$/gdw/h.

The DO may be and preferably is above zero during most of the growth phase, provided that it is reduced to approximately zero at the end of the phase. Thus, an excess of oxygen over that required to maintain the required OUR may be introduced into the medium during most of the growth phase, particularly during the period during which the cells experience exponential growth. As the total oxygen uptake increases during the growth phase as the cells reproduce and biomass accumulates, the total amount of oxygen required to maintain a constant OUR will increase. However, because DO may be positive prior to the end of the growth phase, a preferred way of conducting the aeration is to supply an excess of the required oxygen at the beginning and during the exponential stage of the growth phase. As biomass accumulates, the total oxygen consumed by the cells increases to the point where supplied oxygen closely matches that consumed by the cells, and DO drops as a result. Constant aeration conditions can therefore be used during the growth phase, if those conditions are selected such that DO drops to zero with the required OUR when the desired amount of biomass has been produced. Alternatively, aeration conditions can be varied during the growth phase, provided that the OUR is maintained and DO becomes approximately zero at the end of the growth phase.

Once DO drops to approximately zero and the desired amount of biomass has been produced, it is preferred to maintain those aeration conditions (OUR at least 10 mmol $O_2$/gdw/h and DO equal to zero) for a period of time prior to switching to the production phase. A suitable period of time is about 15 minutes to 2 hours and a preferred period of time is about 30 to 90 minutes. A most preferred period of time is about 45-75 minutes. If the organism is switched to production phase too quickly, the cells tend to exhibit poor production rates. If these aeration conditions are maintained for too long, the cells tend to exhibit poor yields to the desired fermentation product as well as poor production rates.

The culture is switched to production phase through a change in aeration conditions. In the production phase, microaeration conditions are selected such that the OUR is maintained within a predetermined range, as discussed above. Some microorganisms appear to need to metabolize a small amount of oxygen in order to promote overall cell vitality and health. Examples of such organisms include genetically engineered yeast having a PDC disruption, particularly those having an exogenous gene that enables them to produce a particular fermentation product. In fully anaerobic conditions, the rates of substrate consumption and fermentation product production exhibited by these cells are usually very low. In addition, yields of the desired fermentation product suffer. Under microaerobic conditions, at certain OUR values that depend on the particular strain, the cells are able to metabolize the substrate much more rapidly. This results in increased rates of substrate consumption and production of the desired fermentation product. However, as oxygen consumption increases past a certain value, yields to the desired product decrease as more of the substrate is converted to carbon dioxide. In addition, production rates tend to flatten out or even decrease as OUR increases past a certain value, so that yield losses are not compensated for by increased rates. Accordingly, maintaining the OUR within certain ranges during the production phase allows one to achieve an economically optimal balance of yields and production rates.

The optimal value of OUR depends somewhat on the particular organism, although in general, the OUR range is from about 0.8 to about 3 mmol $O_2$/gdw/h. Optimal OUR values for a particular organism are easily determined empirically. A preferred lower end of the OUR range is about 1.0 mmol $O_2$/gdw/h and more preferably about 1.2 mmol $O_2$/gdw/h. A preferred upper end of the OUR range is about 2.5 mmol $O_2$/gdw/h, more preferably about 2.0 mmol $O_2$/gdw/h.

The OUR exhibited by a culture depends largely on the microorganism itself and the aeration conditions. Aeration conditions affect the amount of oxygen that becomes dissolved in the medium and thus becomes available to the organism. For a given organism, increased OUR is favored by (1) increasing the rate at which oxygen is supplied and (2) the formation of small oxygen bubbles (to improve mass transfer of oxygen molecules into the liquid phase. Small bubble formation is readily achieved through sparging and/or agitation.

Examples of aeration rates during the growth phase are about at least 0.2 volumes of air/volume of fermentation medium/minute (vvm), preferably from about 0.3 to about 2 vvm, even more preferably about 0.4 to about 1 vvm. In the production phase, volumes of about 0.01 to about 0.1 vvm, preferably about 0.02 to about 0.75 vvm, especially about 0.02 to about 0.5 vvm are generally suitable. If oxygen is used as the aeration gas, volumes will be proportionately smaller. Aeration is preferably done under conditions such as sparging that promote the formation of fine gas bubbles. Agitation is preferably maintained, particularly when high OUR values are desired. Typically, aeration rates and agitation conditions are selected together in order to achieve the desired OUR.

When the fermentation product is an acid, the medium is buffered during the production phase so that the pH is maintained in a range of about 5.0 to about 9.0, preferably about 5.5 to about 7.0. Suitable buffering agents are basic materials that neutralize lactic acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

Other fermentation conditions, such as temperature, cell density, selection of substrate(s), selection of nutrients, and the like are not considered to be critical to the invention and are generally selected to provide an economical process. Temperatures during each of the growth phase and the production phase may range from above the freezing temperature of the medium to about 50° C., although the optimal temperature will depend somewhat on the particular microorganism. A preferred temperature, particularly during the production phase, is from about 30-45° C. When the cell is an engineered *K. marxianus*, it can tolerate relatively high temperatures (such as above 40° C. and up to 50° C., especially up to 45° C.). Another preferred species of cell, *C. sonorensis*, can tolerate temperatures up to about 40° C. This temperature range provides for the possibility of conducting the fermentation at such higher temperatures (thereby reducing cooling costs) without a significant loss of productivity. Another advantage provided by the good high temperature tolerance is that if the fermentation becomes contaminated with an undesired microorganism, in many cases the undesired microorganism can be selectively killed off by heating the fermentation medium to 40° C. or more, especially 45° C. or more, without significantly harming the desired cells of the invention.

During the production phase, the concentration of cells in the fermentation medium is typically in the range of about 1-150, preferably about 3-10, even more preferably about 3-6 g dry cells/liter of fermentation medium.

The particular carbohydrates that are used depend on the particular host cell, and whether the host cell has been engineered to metabolize any particular carbohydrate to pyruvate. Hexose sugars such as glucose, fructose, glucose oligomers such as maltose, isomaltose, maltotriose, starch and maltodextrins are preferred. In case of oligomeric sugars, it may be necessary to add enzymes to the fermentation broth in order to digest these to the monomeric sugar. An example of a suitable pentose sugar is xylose. Glucose is most preferred.

In a buffered fermentation, acidic fermentation products such as lactic acid are neutralized as they are formed to the corresponding lactate salt. Recovery of the acid therefore involves regenerating the free acid. This is typically done by removing the cells and acidulating the fermentation broth with a strong acid such as sulfuric acid. A salt by-product is formed (gypsum in the case where a calcium salt is the neutralizing agent and sulfuric acid is the acidulating agent), which is separated from the acid. The acid is then recovered through techniques such as liquid-liquid extraction, distillation, absorption, etc., such as are described in T. B. Vickroy, Vol. 3, Chapter 38 of *Comprehensive Biotechnology*, (ed. M. Moo-Young), Pergamon, Oxford, 1985; R. Datta, et al., *FEMS Microbiol. Rev.*, 1995; 16:221-231; U.S. Pat. Nos. 4,275,234, 4,771,001, 5,132,456, 5,420,304, 5,510,526, 5,641,406, and 5,831,122, and International Patent Application No: WO 93/00440.

The medium will typically contain nutrients as required by the particular cell, including a source of nitrogen (such as amino acids proteins, inorganic nitrogen sources such as ammonia or ammonium salts, and the like), and various vitamins, minerals and the like.

The process of the invention can be conducted continuously, batch-wise, or some combination thereof.

The microorganism used in the process of the invention is any that (1) ferments a carbohydrate to a desired fermentation product and (2) ferments more efficiently in the presence of microaerobic conditions than in strictly anaerobic conditions. Cells of particular interest are certain genetically engineered yeast cells characterized by having (1) a disrupted PDC pathway and (2) at least one functional exogenous gene that enables the cell to produce the desired fermentation product. Suitable such engineered yeast cells are described, for example, in Porro et al., "Development of metabolically engineered *Saccharomyces cerevisiae* cells for the production of lactic acid", *Biotechnol. Prog.* 1995 May-June; 11(3): 294-8; Porro et al., "Replacement of a metabolic pathway for large-scale production of lactic acid from engineered yeasts", *App. Environ. Microbiol.* 1999 September:65(9):4211-5; Bianchi et al., "Efficient homolactic fermentation by *Kluyveromyces lactis* strains defective in pyruvate utilization and transformed with the heterologous LDH gene", *App. Environ. Microbiol.* 2001 December; 67(12)5621-5; WO 00/71738, WO 02/42471, PCT/US02/16223, and U.S. provisional application No. 60/384,333, filed May 30, 2002. The cell also preferably exhibits the Crabtree negative phenotype, so that it respires and grows under aeration conditions in the presence of high concentrations of glucose and at high specific growth rates.

By "disrupted", it is meant that a native PDC pathway has been altered so that function of the PDC pathway is reduced by at least 90%. Disruption may be achieved by altering the pathway (or one or more genes associated with the pathway) so that it its function is reduced or eliminated, or by removing one or more genes required for the pathway to function. A preferred cell has a deletion of a PDC gene.

A preferred exogenous gene is a lactate dehydrogenase (LDH) gene. The gene is preferably integrated into the genome of the cell. The engineered yeast cell may have a single copy or multiple copies of the exogenous LDH gene. It may contain two or more different exogenous LDH genes. In an especially preferred embodiment, the gene is integrated into the genome of the cell at the location of a native PDC gene, which is deleted. In the especially preferred embodiment, the LDH gene is under the functional control of operative promoter and terminator sequences that are at least 90% homologous to promoter and terminator sequences (particularly PDC promoter and terminator sequences) that are native to the cell. These preferred and especially preferred cells are described more fully in U.S. Provisional Application No. 60/384,333, filed May 30, 2002 and incorporated herein by reference.

*Lactobacillus helveticus, Pediococcus acidolactici, Lactobacillus casei, Kluyveromyces thermotolerans, Torulaspora delbrueckii, Schizosaccharomyces pombii* and *B. megaterium* are strains that have suitable L-lactate dehydrogenase genes that can be cloned for use in producing the engineering yeast. Two preferred L-lactate dehydrogenase genes are *L. helveticus* and *B. megaterium* L-lactate dehydrogenase. *Lactobacillus helveticus, Lactobacillus johnsonii, Lactobacillus bulgaricus, Lactobacillus delbrueckii, lactobacillus plantarum* and *Lactobacillus pentosus* are strains that have suitable D-lactate dehydrogenases that can be cloned for use in the engineered yeast. A preferred D-lactate dehydrogenase gene is *L. helveticus* D-lactate dehydrogenase.

To be commercially useful, the engineered cell should exhibit several characteristics. The yeast should convert a significant proportion of the carbohydrate to the desired fermentation product (i.e., produce a high yield of product). It should exhibit a high specific productivity, i.e., product a high amount of fermentation product per weight of cell per unit time. The cell is preferably also tolerant to high concentrations of the fermentation product. This last property allows the fermentation process to use high concentrations of the starting carbohydrate.

In general, it is desirable that the fermentation process of the invention provides some or all of the following features:

A. A yield of at least 30, preferably at least 40, more preferably at least 60, even more preferably at least 75 grams of fermentation product per gram of substrate. The theoretical desired yield is 100%, but practical limits on yields are about 98%.

B. A specific productivity of at least 0.1, preferably at least 0.3, more preferably at least about 0.4, especially at least about 0.5 grams of fermentation product/gram of cells/hour. Specific productivities are desirably as high as possible.

C. A titer (maximum concentration of fermentation product) of at least 15 grams/liter of fermentation medium, preferably at least 20 g/L, more preferably at least 40 g/L, even more preferably at least 80 g/L, up to 150 g/L, preferably up to about 120 g/L. In the case of lactic acid, the temperature of the fermentation medium affects the high end of readily achievable titers somewhat, as highly concentrated lactic acid solutions (i.e., above about 150 g/liter) tend to become very viscous or gel at temperatures below about 35° C. Using a higher fermentation temperature, such as from about 35-50° C., permits higher titers without gelling or undue viscosity build-up.

In addition, the fermentation process of the invention preferably achieves a high volume productivity. Volume productivity is expressed as amount of product produced per unit volume of fermentation medium per unit time, typically gram of product/liter medium/hr of time. Volume productivities of at least 1.5 g/L/hr, preferably at least 2.0 g/L/hr, more preferably at least 2.5 g/L/hr are desirable. At preferred cell densities of up to 3-6 g cells/liter of fermentation medium, maximum productivities tend to up to about 5.0 g/L/hr, and more typically up to about 4.0 g/L/hr. It is highly preferred to conduct the fermentation so that these volume productivities are achieved when the medium pH, temperature, or both are within the ranges described in the preceding paragraph.

Lactic acid produced according to the invention is useful to produce lactide, a cyclic anhydride of two lactic acid molecules. Depending on the stereoisomer of the lactic acid, the lactide may be D-lactide (made from two D-lactic acid molecules), L-lactide (made from two L-lactic acid molecules) or D-L-lactide (made from one of each L-lactic acid and D-lactic acid molecules). A convenient method of producing lactide from lactic acid is via a polymerization/depolymerization method as described in U.S. Pat. No. 5,142,023 to Gruber et al.

Lactide, in turn, is particularly useful as a monomer for the production of polylactide polymers (PLA) and copolymers. Processes for preparing these polymers are also described in U.S. Pat. No. 5,142,023 to Gruber et al. Preferred PLA products are melt-stable polymers as described in U.S. Pat. No. 5,338,822 to Gruber et al. The PLA may be semi-crystalline or amorphous.

The following examples serve to illustrate certain embodiments of the invention and do not limit it in scope or spirit. All parts and percentages are by weight unless otherwise indicated.

EXAMPLE 1

An inoculation stock of an engineered yeast cell designated CD 587 is prepared in a 250 ml shake flask containing 100 ml $CaCO_3$-buffered (42 g/l) yeast extract (10 g/l)—peptone (20 g/l) medium with 100 g/l glucose. At $OD_{600}$=10, the cells are harvested by centrifugation and subsequently resuspended in 15% (w/v) glycerol solution and stored in 1.5 mL aliquots at −80° C.

Cell CD 587 is a K. marxianus cell having its PDC gene deleted and an exogenous L. helveticus D-LDH gene integrated into its genome at the site of the deleted PDC gene, under the control of native PDC promoter and terminator sequences. Cell CD 587 and its preparation are described more fully in U.S. Provisional Application No. 60/384,333, filed May 30, 2002.

The growth phase is started by inoculating a 3 L fermenter with one 1.5 mL glycerol stock, resulting in an initial $OD_{600}$ of 0.05. The growth phase is run aerobically by continually sparging air at a flow rate of 1.5 L/min (0.5 vvm) at a constant stirrer speed of 800 rpm. Growth is continued until the DO is reduced to 5% of air saturation. This coincides with a constant $CO_2$ concentration in the off-gas. OUR is measured by monitoring the amount of air supplied and analyzing the off-gases for oxygen using mass spectrometry. During the growth phase, the OUR is about 20.8±2.5 mmol $O_2$/gdw/hr. Under these conditions, OUR is limited by the ability of the cell to metabolize available oxygen. Final cell density is about 4 g/L.

Once DO reaches zero, aeration conditions are maintained for one hour before starting the production phase. The production phase is initiated by instantaneously switching the airflow rate to 0.1 L/min (0.033 vvm) and decreasing the stirrer rate to 500 rpm. This change in aeration conditions results in an OUR of 1.5±0.1 mmol $O_2$/gdw/hr and a DO of zero during the production phase. The fermentation is continued for about 60 hours. The glucose consumption rate, lactate production rate and yield to lactate are measured by periodically removing samples for HPLC/IC/GC-MS analysis. Results in the production phase are as shown in Table 1.

TABLE 1

| | |
|---|---|
| Maximum Lactic Acid Titer | 106 ± 3.1 g/kg |
| Glucose Consumption Rate | 1.2 ± 0.05 g/gdw/h |
| Lactic Acid Production Rate | 1.1 ± 0.04 g/gdw/h |
| Yield to Lactic Acid (production phase) | 0.92 ± 0.03 g Lactic Acid/g Glucose |
| % Carbon Recovered (production phase) | 99% ± 3.0 |
| Optical Purity of the Lactic Acid | >99.9 |

This experiment is repeated several times, varying the aeration conditions in the production phase so as to effect OUR values of about 1.2, 2.2, 2.8, 3.0 and 3.2 in successive runs. Results are shown graphically in FIG. 1. As shown in FIG. 1, yield (curve 1) decreases steadily and dramatically with increasing OUR through the range of 1.2 to 3.0, where an increase (possibly an anomaly) is seen before a further significant decrease at an OUR of 3.2. These decreased yields are consistent with increased cell respiration as oxygen is increasingly available. Lactate production rates (curve 3) increase slightly within an OUR range of 1.2 to about 2.2 and then fall off as OUR is increased to 2.8 before increasing. However, the benefit of increased production rates at OUR values of 3 or more is lost due to the increasing yield loss. Glucose utilization rates (curve 2) increase somewhat as OUR increases from 1.2 to 2.8 and increase substantially at an OUR above 3.0 due to rapid cell respiration. The data in FIG. 2 suggests that for this strain, an optimum OUR value is in the range of about 0.8 to 2.2, and especially from about 1.0 to about 1.5.

EXAMPLE 2

Example 1 is repeated several times using a strain designated CD 558. Strain CD 558 is a K. marxianus cell having its PDC gene deleted. It contains an exogenous L. helveticus D-LDH gene randomly integrated into its genome. The LDH gene is under the control of a S. cerevisiae PGK-1 promoter and S. cerevisiae Gal-10 terminator sequences. In each run, OUR in the growth phase is about 20.5 mmol $O_2$/gdw/hr. Aeration conditions during the production phases are varied from run to run by controlling sparging and stirring rates, in order to vary OUR. OUR values for the different runs are about 0.6, 1.4, 1.7 and 2.2. At a production phase OUR of 1.7, results are as shown in Table 2:

TABLE 2

| | |
|---|---|
| Maximum Lactic Acid Titer | 111 g/kg |
| Glucose Consumption Rate | 0.94 g/gdw/h |
| Lactic Acid Production Rate | 0.83 g/gdw/h |

TABLE 2-continued

| | |
|---|---|
| Yield to Lactic Acid (production phase) | 0.89 g Lactic Acid/g Glucose |
| % Carbon Recovered (production phase) | 95.6 |
| Optical Purity of the Lactic Acid | >99.9 |

Figure 2:
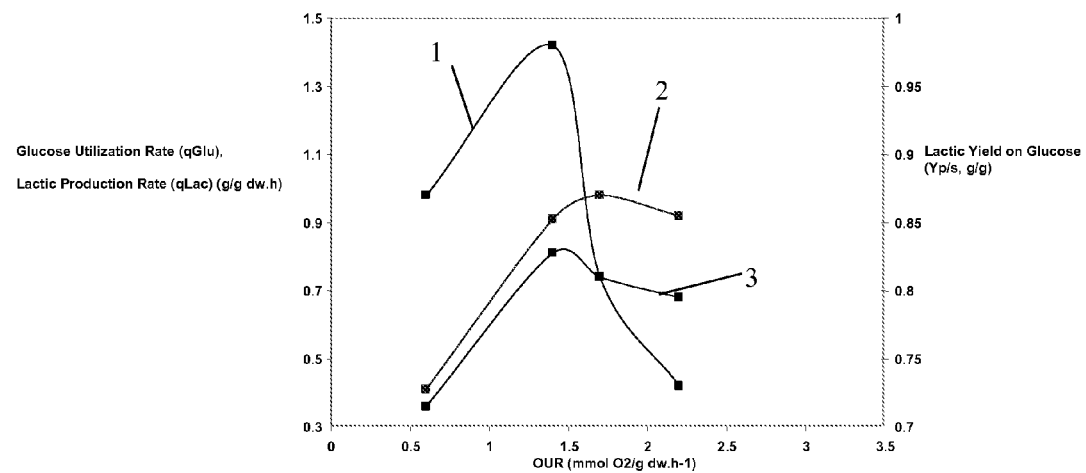
FIG. 2 is a graph illustrating the effect of OUR on glucose consumption, lactic acid production and yield for another genetically modified *K. marxianus* species.

FIG. 2 illustrates how varying OUR affects production rates and yields. For this strain, yield to lactic acid (curve 1) exhibits a very strong dependence on OUR in the range of 0.7 to 2.2, achieving a maximum when the OUR is around 1.4. Lactate production rates (curve 3) similarly peak at that OUR value. Glucose consumption rates (curve 2) increase until the OUR is about 2.2 and then flatten out. For this strain, the data in FIG. 2 suggests that the optimum OUR is in the range of about 1 to about 1.7, especially about 1.2-1.5.

EXAMPLE 3

Example 1 is repeated three times. The first of these runs (3A) is conducted as described in Example 1, except OUR during the production phase is 2.1 mmol $O_2$/gdw/h. During the second of these runs (3B), the culture is switched to production phase immediately when the DO during the growth phase reaches zero. OUR is 1.8 mmol $O_2$/gdw/h, under the same aeration conditions as Example 3A. In the third run (3C), aeration is continued at the end of the growth phase for over 1.5 hours after the DO reaches zero, and the OUR in the production phase is 1.4 mmol $O_2$/gdw/h under the same aeration conditions as Example 3A. Results are summarized in Table 3

TABLE 3

| | Example No. | | |
|---|---|---|---|
| Property | 3A | 3B | 3C |
| Holding time, zero DO | 1 hr | 0 | >1.5 hr |
| OUR, production phase (mmol/gdw/h) | 2.1 | 1.8 | 1.4 |
| Maximum Lactic acid titer (g/kg) | 112.3 | 84 | 94 |
| Glucose consumption rate (g/gdw/h) | 1.22 | 1.06 | 0.40 |
| Lactate production rate (g/gdw/h) | 1.20 | 0.93 | 0.32 |
| Yield Lactic acid (production phase, g/g) | 0.89 | 0.84 | 0.79 |
| % carbon recovery (production phase) | 105 | 104.3 | 98 |
| Optical Purity (%) | >99.9 | >99.9 | >99.9 |

Under given aeration conditions during production, OUR is an indicator of the metabolic activity of the microorganism. The decrease in OUR when the holding time is zero or exceeds 1.5 hr (relative to that after a holding period of 1 hour) indicates that the microorganism functions less well under those conditions. This is also reflected in a decrease in glucose consumption, lactate production and yields.

EXAMPLE 4

An inoculation stock of yeast cell CD 587 is cultivated aerobically in a 14-liter laboratory bioreactor using a buffered (pH 5.5) mineral medium supplemented with 160 g/l glucose. Aeration is supplied by sparging air with agitation at a rate of 5 liters/minute. The DO during this initial growth phase is initially 100% and decreases to 20% during the cycle. OUR is maintained at about 20 mmol $O_2$/gdw/h. When the $OD_{600}$=10, 4 liters of the broth are transferred to as 240 liter production-scale fermenter containing an additional 220 liters of the growth medium supplemented with 170 g/l glucose. The cells are grown further under aerobic conditions at a temperature of 42° C. and pH of 5.5 for about 8 hours. DO is reduced from a starting value of 100 down to zero during this time. OUR is maintained at 20 mmol $O_2$/gdw/h by aeration with 15 liters/minute of air. The culture is maintained at DO zero for one hour. The culture is then switched to production phase by reducing aeration to achieve an OUR of 1.5-1.7 mmol $O_2$/gdw/h. Additional buffering agent ($Ca(OH)_2$ is added on demand to maintain the pH at 5.5±0.1. DO remains at 0% during the production phase. The glucose is consumed within 30 hours, providing a lactate titer of 114 g/kg. The mean specific glucose consumption rate during the production phase is 1.1 g/g DW.h-1. The mean specific lactic acid production rate is 0.8 g/g DW.h-1 with a production yield of 0.76 g lactic acid/g. glucose and an overall yield (including the growth phase) of 0.67 g lactic acid/g glucose.

What is claimed is:
1. A fermentation process comprising
   a) growing engineered yeast cells of the genus Kluyveromyces in a medium comprising a carbohydrate that the cells are capable of metabolizing, while aerating the medium such that as the cells grow and reproduce the dissolved oxygen tension in the medium is reduced to zero and the cells exhibit a specific oxygen uptake rate (OUR) of at least 10 mmol $O_2$/g dry weight of cells/hour (mmol $O_2$/gdw/h); and then
   b) culturing the cells in a buffered medium under fermentation conditions including microaeration conditions sufficient to provide the culture with a specific oxygen uptake rate of about 0.8 to about 3.0 mmol $O_2$/gdw/h.
2. The process of claim 1, wherein the carbohydrate includes a hexose sugar.
3. The process of claim 2, wherein the hexose sugar includes glucose.
4. The process of claim 1, wherein the yeast cells have a disrupted PDC pathway.

* * * * *